United States Patent Office

Plant Pat. 2,702
Patented Jan. 24, 1967

2,702
APPLE TREE

Frank H. McDermid, deceased, late of Pennfield Township, Calhoun County, Mich., by James A. McDermid, administrator, Pennfield Township, Calhoun County, Mich., assignor to Stark Bro's Nurseries & Orchards Co., Louisiana, Mo., a corporation of Missouri Filed Dec. 21, 1965, Ser. No. 515,808
1 Claim. (Cl. Plt.—34)

The present invention relates to a new and distinct variety of apple tree which was discovered by the late Frank H. McDermid as a newly found seedling of unknown parentage, on property owned by him in Pennfield Township, Calhoun County, Michigan.

At the time of his discovery, his attention was attracted to the new variety in the course of a routine inspection of his orchard, by reason of the fact that the fruit appeared to be different than that of any other variety then being cultivated by him. He thereupon took steps to preserve the originally-discovered tree, keep it under observation and to later asexually reproduce the same by grafting in his own orchard on the property aforementioned. Continued observations of the original tree and of the progeny thereof as asexually reproduced by him and also on his behalf in Pike County, Missouri, have conclusively established that the new variety bears fruit resembling the variety known as "Beacon" (unpatented) in general appearance and ripening season, but differs essentially from the variety "Beacon" by its larger foliage which is a slightly lighter shade of green color, and by its attractive fruit of excellent quality which has a shallower basin, a longer and more slender stem, an open core instead of a closed core like the fruit of "Beacon," and a very much superior fruit flavor.

While the actual parentage of the new variety is not known, it is definitely differentiated from all other varieties of which he was aware, and the characteristics and distinctions referred to in the foregoing represent a unique and desirable combination which is particularly valuable from a commercial standpoint.

The accompanying drawing shows typical specimens of the foliage and fruit of the new variety as depicted in color as nearly true as it is reasonably possible to make the same in a color illustration of this character, certain of said fruit specimens depicting the exterior shape and coloring of the fruit, while another specimen shows a cross-section to illustrate interior details thereof.

The following is a detailed description of the new variety, with color terminology in accordance with Ridgway's Color Standards and Nomenclature (hereinafter abbreviated (R)) or the Horticultural Colour Guide (hereinafter abbreviated (HCG)) or the Nickerson Color Fan, published by Munsell Color Company, Inc., of Baltimore, Maryland (hereinafter abbreviated (N)), as indicated, except where general color terms of ordinary dictionary significance are obvious:

(Observations made from specimens grown at Louisiana, Pike County, Missouri.)

Dates of first and last pickings: About August 1st and Augusta 7th, respectively; ripens about same time as "Beacon."

Tree: Medium-large; vigorous; spreading; round-topped; rapid growing; hardy; productive; regular bearer.

*Trunk.*—Medium-stocky; smooth.

*Branches.*—Medium thickness; smooth; little-branching. Color—Dresden Brown, Plate XV, Color No. 17', Tone *k* R). Lenticels—medium number; small.

*Leaves.*—Medium-large; medium length; medium width; oval; abruptly pointed; thick; smooth.

Length—about 4 inches. Width—about 2⅜ inches. Color—Spinach Green, Plate 0960/1, page 187, volume 2 (HCG). Margin—finely serrate. Petiole—medium length; medium thickness; length—about 1⅜ inches.

Flowers:

*Dates of first and full bloom.*—About April 23rd and May 3rd, respectively; medium-early as compared with other varieties.

*Size.*—Medium-large.

*Color.*—White, with segments of lower (outer) side Deep Purplish-Pink, Plate 5RP 6/10 (N).

Fruit:

*Maturity when described.*—Eating-ripe; about July 28th.

*Size.*—Uniform. Axial diameter—about 2½ inches. Transverse diameter—about 2⅞ inches.

*Form.*—Round-conical; ribbed.

*Cavity.*—Symmetrical; rounded at base; apex acute; undulate toward apex. Depth—about ⅜ inch. Breadth—about ⅞ inch. Markings—color—Pod Green, Plate 061/1, page 120, volume 2 (HCG).

*Basin.*—Symmetrical; base flaring, wide-furrowed and pubescent. Depth—about ⅛ inch. Breadth—about ¾ inch.

*Stem.*—Medium-stout; pubescent. Length—about ¾ inch. Breadth—about 3/32 inch.

*Calyx.*—Closed; segments persistent; narrowly lanceolate; acuminate; erect; reflexed from base at apex. Length—about 3/16 inch. Outer surface—pubescent. Inner surface—pubescent.

*Skin.*—Thick; tough; smooth; glossy; waxed. Dots—obscure; many; small; even; circular; color—Cartridge Buff, Plate XXX, Color No. 19". Tone *f* (R); distribution—over all; more numerous toward base. Ground color—Pea Green, Plate 61/1, page 61, volume 1 (HCG). Color markings—striped; bright; color—Rhodonite Red, Plate 0022, page 188, volume 2 (HCG), nearly covered with stripes and blush of Spinel Red, Plate 0023, page 189, volume 2 (HCG).

*Bloom.*—Scant.

*Scarfskin.*—Wanting.

*General color effect.*—Attractive bright red.

*Flesh.*—Juicy. Color—satiny white, with greenish tint. Texture—firm; tender; fine; crisp. Flavor—subacid. Aroma—wanting. Quality—good.

*Core.*—Median. Bundle area—large; orbicular; unsymmetrical at base. Halves of core—unequal. Bundles—inconspicuous; in one whorl; color—Pea Green, Plate 61/1, page 61, volume 1 (HCG). Core lines—clasping; indistinct in cross-section. Carpellary area—indistinct; small. Calyx tube—glabrous; apex narrowly obconic; entire depth—about ¼ inch. Styles—present; united; distinct toward base pubescent. Stamens—in one whorl; marginal. Seed cells—axil; open; cell walls—distant; thin; length—about ⅞ inch; breadth—about ⅜ inch; longitudinal section—narrowly ovate; obtuse at apex; surface—fissured; cross section—medium-narrow.

Seeds:

*Average number.*—From 7 to 9 perfect; from none to 2 imperfect; usually 2 seeds per cell. Length—about ⅜ inch. Breadth—about 5/32 inch.

*Color.*—Roods Brown, Plate XXVIII, Color No. 11", Tone *k* (R).

Use: Market; good for summer variety.

Keeping quality: About 12 days in ordinary storage.

What is claimed is:

A new and distinct variety of apple tree, substantially as herein shown and described, characterized particularly as to novelty by its habit of bearing fruit which generally resembles the fruit of "Beacon" (unpatented) in general appearance and time of ripening, but essentially differing from "Beacon" by its larger foliage which is a slightly lighter shade of green color, and by its attractive fruit of excellent quality which has a shallower basin, a longer and more slender stem, an open core instead of a closed core like the fruit of "Beacon," and a very much superior fruit flavor.

No references cited.

ABRAHAM G. STONE, *Primary Examiner.*

ROBERT E. BAGWILL, *Examiner.*

Jan. 24, 1967 F. H. McDERMID Plant Pat. 2,702
APPLE TREE
Filed Dec. 21, 1965
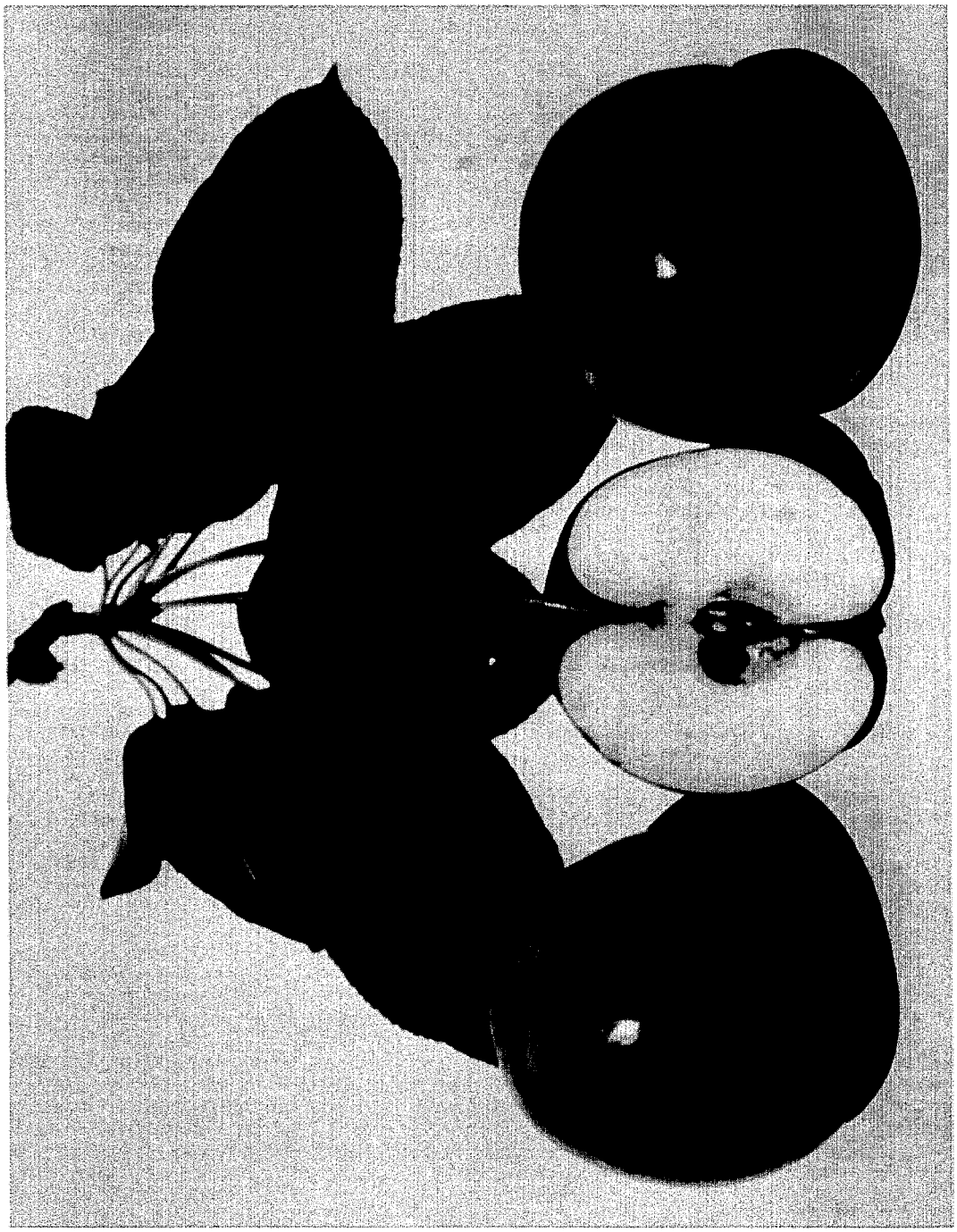
Inventor.
Frank H. McDermid, Deceased
By: James A. McDermid, Administrator
By: Robb & Robb
Attorneys.